US010758458B2

(12) United States Patent
Gross et al.

(10) Patent No.: US 10,758,458 B2
(45) Date of Patent: Sep. 1, 2020

(54) BONDABLE MICROCAPSULES AND SURFACE FUNCTIONALIZED FILLERS

(71) Applicant: PREMIER DENTAL PRODUCTS COMPANY, Plymouth Meeting, PA (US)

(72) Inventors: Stephen M. Gross, Omaha, NE (US); William A. McHale, Collegeville, PA (US); Mark A. Latta, Omaha, NE (US)

(73) Assignee: Premier Dental Products Company, Plymouth Meeting, PA (US)

(*) Notice: Subject to any disclaimer, the term of this patent is extended or adjusted under 35 U.S.C. 154(b) by 0 days.

(21) Appl. No.: 15/513,526

(22) PCT Filed: Sep. 24, 2015

(86) PCT No.: PCT/US2015/051931
§ 371 (c)(1),
(2) Date: Mar. 22, 2017

(87) PCT Pub. No.: WO2016/049308
PCT Pub. Date: Mar. 31, 2016

(65) Prior Publication Data
US 2017/0296440 A1 Oct. 19, 2017

Related U.S. Application Data

(60) Provisional application No. 62/055,127, filed on Sep. 25, 2014.

(51) Int. Cl.
A61K 6/083 (2006.01)
A61K 6/093 (2006.01)
C08F 290/06 (2006.01)
B01J 13/16 (2006.01)
A61K 6/00 (2020.01)
C08G 18/81 (2006.01)
A61K 6/887 (2020.01)
A61K 33/18 (2006.01)
A61K 31/14 (2006.01)
A61K 31/4425 (2006.01)
C01B 9/08 (2006.01)
C08G 18/67 (2006.01)
C08G 18/72 (2006.01)
C08G 18/32 (2006.01)
A61K 6/62 (2020.01)
A61K 6/69 (2020.01)
A61K 6/72 (2020.01)
A61K 6/74 (2020.01)
A61K 6/77 (2020.01)
A61K 6/893 (2020.01)
A61K 6/896 (2020.01)

(52) U.S. Cl.
CPC ............. A61K 6/887 (2020.01); A61K 6/62 (2020.01); A61K 6/69 (2020.01); A61K 6/72 (2020.01); A61K 6/74 (2020.01); A61K 6/77 (2020.01); A61K 6/893 (2020.01); A61K 6/896 (2020.01); A61K 31/14 (2013.01); A61K 31/4425 (2013.01); A61K 33/18 (2013.01); B01J 13/16 (2013.01); C01B 9/08 (2013.01); C08F 290/067 (2013.01); C08G 18/3203 (2013.01); C08G 18/672 (2013.01); C08G 18/72 (2013.01); C08G 18/8175 (2013.01)

(58) Field of Classification Search
CPC ... A61K 6/74; A61K 6/69; A61K 6/72; A61K 6/62; A61K 6/0091; C08G 18/672; C08G 18/8175; C08F 290/067
See application file for complete search history.

(56) References Cited

U.S. PATENT DOCUMENTS

| 4,780,390 A | * | 10/1988 | Hosoi | G03G 9/09342 428/402.2 |
| 5,132,117 A | * | 7/1992 | Speaker | A61K 9/5089 264/4.1 |
| 6,244,274 B1 | * | 6/2001 | Sirdesai | A45D 31/00 132/200 |
| 2003/0157023 A1 | | 8/2003 | Roessling et al. | |
| 2004/0007784 A1 | | 1/2004 | Skipor et al. | |
| 2005/0026801 A1 | * | 2/2005 | Broeckx | B01J 13/02 510/276 |
| 2009/0012209 A1 | | 1/2009 | Eckhardt et al. | |
| 2009/0221419 A1 | * | 9/2009 | Pears | B01J 13/16 502/159 |
| 2010/0087611 A1 | * | 4/2010 | Urakawa | C08G 18/3853 526/261 |
| 2010/0272764 A1 | * | 10/2010 | Latta | A61K 8/11 424/401 |
| 2011/0104052 A1 | * | 5/2011 | Barnett | A61K 9/0019 424/1.21 |
| 2013/0011453 A1 | | 1/2013 | Latta et al. | |

FOREIGN PATENT DOCUMENTS

| CN | 1718632 A | 1/2006 | |
| CN | 103118651 A | 5/2013 | |
| EP | 2363109 A2 * | 9/2011 | ............... A61K 8/35 |
| JP | 2004-517820 A | 6/2004 | |
| JP | 2005289961 A * | 10/2005 | |
| WO | WO 99-59554 | 11/1999 | |
| WO | WO 2014-043385 | 3/2014 | |

OTHER PUBLICATIONS

Sigma-Aldrich product information (camphorquinone), obtained online via www.sigmaaldrich.com. (Year: 2018).*
Sigma-Aldrich product information (ethyl-4-dimethylamino-benzoate), obtained online via www.sigmaaldrich.com. (Year: 2018).*
Search Report dated Apr. 4, 2018 which issued in the corresponding European Patent Application No. 15843335.9.

* cited by examiner

Primary Examiner — Mina Haghighatian
(74) Attorney, Agent, or Firm — Vos-IP, LLC

(57) ABSTRACT

A composition comprising microcapsules functionalized with polymerizable functional groups on the surface of said microcapsules wherein the functional groups form covalent bonds with monomers in the continuous phase to enhance the mechanical properties of the composition.

14 Claims, 6 Drawing Sheets

Step 1: Preperation of surface funtionalized shell material excess OCN-R-NCO + HO-R-OH ⟶ OCN-(RNHCO$_2$-R-)$_n$-NCO + HOR-vinyl vinyl terminated - (RNHCO$_2$-R-)$_n$-vinyl terminated

Step 2: Preperation of surface funtionalized microcapsule

Mix surface functionalized shell material, emulsifying agent, oil phase. Agitate mixture, with or without heat. Add an aqueous phase or other liquid phase (silicone). Perform an interfacial polymerization of the urethane in the surfactant free inverse emulsion. Isolate surface functionalized microcapsule.

Step 3: Formulation of surface funtionalized microcapsule

Combine surface functionalized microcapsule with desired continuous phase monomers and initiator. The surface functional group should be polymerizable with the monomer to create covalent link between the filler and continuous phase.

FIG. 1

BONDABLE MICROCAPSULES AND SURFACE FUNCTIONALIZED FILLERS

PRIORITY CLAIM

This is a U.S. national stage of application No. PCT/US2015/051931, filed on Sep. 24, 2015. This application claims priority from U.S. Provisional Patent Application Ser. No. 62/055,127 which was filed on Sep. 25, 2014.

FIELD OF INVENTION

The present application is generally related to compositions, methods and products useful for composite materials comprising microcapsules. The compositions comprise microcapsules with polymerizable functional groups added to monomeric or polymeric continuous phases that enhance the mechanical properties of the composite. Further, the microcapsules can be filled with liquid phases that further improve the mechanical properties of the composite, or render the composite bioactive for applications including, but not limited to, promoting remineralization and imparting antimicrobial activity to the composite.

BACKGROUND OF THE INVENTION

Dental composite materials are utilized in many cases to fill caries and to improve tooth health. At one time, metal-based amalgams, then porcelain or other ceramic materials were used in a variety of remedial dental procedures. Now, synthetic composites are used as practical alternatives to these materials for such procedures. A composite is a polymer, otherwise referred to as a resin, which has at least one additive. An additive can be anything added to the polymer or resin to impart a desired property. The composite generally starts out as a paste or liquid and begins to harden when it is activated, either by adding a catalyst, adding water or another solvent, or photoactivation. Advantageously, synthetic composites provide an aesthetically more natural appearance versus porcelain or other ceramic materials.

Synthetic composites are typically made from complex mixtures of multiple components. Synthetic composites must be completely dissolvable in a fluid vehicle, yet remain flowable and viscous; undergo minimal thermal expansion during polymerization; be biocompatible with surrounding surfaces of tooth enamel and colloidal dentin; and, have aesthetic similarity to natural dentition in terms of color tone and polishable texture. Furthermore, the synthetic composite must have sufficient mechanical strength and elasticity to withstand ordinary compressive occlusive forces, without abnormal wearing and without causing abrasion to dentinal surfaces.

The different varieties of synthetic composites may be approximately divided into three main groups of products: synthetic resin-based dental composites, glass-based dental composites, and hybrid dental composites.

A synthetic resin-based dental composite typically comprises several monomers combined together. A monomer is a chemical that can be bound as part of a polymer. The synthetic resin-based dental composite includes other materials, such as silicate glass or processed ceramic that provides an essential durability to the composite. These materials-may also be made from an inorganic material, consisting of a single type or mixed variety of particulate glass, quartz, or fused silica particles. Using differing types of inorganic materials, with differing diameter sizes or size mixtures, results in differing material characteristics.

Glass-based dental composites are made from a glass particles, such as powdered fluoroaluminosilicate, dissolved in an aqueous polyalkenoate acid. An acid/base reaction occurs spontaneously, causing precipitation of a metallic polyalkenoate, which subsequently solidifies gradually. The glass particles may be made from silicate, such as silicone dioxide or aluminum silicate, but may also include an intermixture of barium, borosilicate, alumina, aluminum/calcium, sodium fluoride, zirconium, or other inorganic compounds. Some of the earlier glass-based composites were formulated to contain primarily a mixture of acrylic acid and itaconic acid co-monomers. However, more recently such hybrid products are modified to include other polymerizable components, such as HEMA or BisGMA.

Hybrid composites are the third category of synthetic dental composites. Hybrid composites combine glass particles with one or more polymers. Hybrid composites may comprise water-soluble polymers other than polyalkenoate, such as hydroxyethyl methacrylate (HEMA) and other co-polymerizing methacrylate-modified polycarboxylic acids, which are catalyzed by photo activation. Other hybrid composites may be modified to include polymerizable tertiary amines, catalyzed by reaction with peroxides.

Synthetic dental composites are increasingly used more often for dental procedures, such as restoration and repair. Restoration and repair includes, for example, fillings, crowns, bridges, dentures, orthodontic appliances, cements, posts and ancillary parts for dental implants to name a few. Most common, synthetic dental composites are used for anterior Class III and Class V reconstructions, for smaller size Class I and Class II molar reconstructions, for color-matching of cosmetic veneers, and for cementing of crowns and overlays. Nonetheless certain disadvantages of these materials have been noted. For example, the trace amounts of unconverted monomers and/or catalyst that may remain within the composite and, if subsequently absorbed systemically in humans, may be potentially physiologically harmful.

Another major drawback associated with synthetic composites is that they tend to wear more rapidly, especially when placed in appositional contact with load-bearing dental surfaces, a deficiency that often limits the purposeful use of such materials primarily to repair of defects within anterior maxillary or readily visible mandibular surfaces.

Perhaps the most significant disadvantage associated with synthetic composites is that they have a comparatively lower resistance to fracture. Even relatively minor surface discontinuities within the composite, whether occurring from injurious trauma or occlusive stress, may progressively widen and expand, eventually resulting in partial or complete disintegration of the reconstruction or repair. This greater susceptibility to fracture is thought to be correlated with the dental reconstruction or repair.

Fracture susceptibility is also correlated with the proportional volume of the amount of synthetic composite required, or the lesser fraction of intact enamel and dentinal tooth material that remains available, prior to reconstruction or repair. It is well established from studies of the "cracked tooth syndrome" that once a damaging fracture has occurred, tooth loss may be almost inevitable, especially for carious teeth that have been previously filled. An improved synthetic composite having greater resistance to fracture would be significantly advantageous.

The susceptibility of fracture and damage to bone tissue is relevant to children and adults alike whom require filling of caries in tooth materials. However, it is known that certain changes in bone mass occur over the life span of an individual. After about the age of 40 and continuing to the last stages of life, slow bone loss occurs in both men and women. Loss of bone mineral content can be caused by a variety of conditions, and may result in significant medical problems. If the process of tissue mineralization is not properly regulated, the result can be too little of the mineral or too much—either of which can compromise bone health, hardness and strength. A number of bone growth disorders are known which cause an imbalance in the bone remodeling cycle. Chief among these are metabolic bone diseases such as osteoporosis, osteoplasia (osteomalacia), chronic renal failure and hyperparathyroidism, which result in abnormal or excessive loss of bone mass known as osteopenia. Other bone diseases, such as Paget's disease, also cause excessive loss of bone mass at localized sites.

Osteoporosis is a structural deterioration of the skeleton caused by loss of bone mass resulting from an imbalance in bone formation, bone resorption, or both. Bone resorption is the process by which osteoclasts break down bone and release the minerals, resulting in a transfer of calcium from bone fluid to the blood. Bone resorption dominates the bone formation phase, thereby reducing the weight-bearing capacity of the affected bone. In a healthy adult, the rate at which bone is formed and resorbed is tightly coordinated so as to maintain the renewal of skeletal bone. However, in osteoporotic individuals, an imbalance in these bone remodeling cycles develops which results in both loss of bone mass and in formation of micro-architectural defects in the continuity of the skeleton. These skeletal defects, created by perturbation in the remodeling sequence, accumulate and finally reach a point at which the structural integrity of the skeleton is severely compromised and bone fracture is likely. Although this imbalance occurs gradually in most individuals as they age, it is much more severe and occurs at a rapid rate in postmenopausal women. In addition, osteoporosis also may result from nutritional and endocrine imbalances, hereditary disorders and a number of malignant transformations.

Osteoporosis in humans is preceded by clinical osteopenia (bone mineral density that is greater than one standard deviation but less than 2.5 standard deviations below the mean value for young adult bone), a condition found in approximately 25 million people in the United States. Another 7-8 million patients in the United States have been diagnosed with clinical osteoporosis (defined as bone mineral content greater than 2.5 standard deviations below that of mature young adult bone). Osteoporosis is one of the most expensive diseases for the health care system, costing billions of dollars annually in the United States. In addition to health care related costs, long-term residential care and lost working days add to the financial and social costs of this disease. Worldwide, approximately 75 million people are at risk for osteoporosis.

The frequency of osteoporosis in the human population increases with age, and among Caucasians is predominant in women, who comprise approximately 80% of the osteoporosis patient pool in the United States. In addition in women, another phase of bone loss occurs possibly due to postmenopausal estrogen deficiencies. During this phase of bone loss, women can lose an additional 10% in the cortical bone and 25% from the trabecular compartment. The increased fragility and susceptibility to fracture of skeletal bone in the aged is aggravated by the greater risk of accidental falls in this population. More than 1.5 million osteoporosis-related bone fractures are reported in the United States each year. Fractured hips, wrists, and vertebrae are among the most common injuries associated with osteoporosis. Hip fractures in particular are extremely uncomfortable and expensive for the patient, and for women correlate with high rates of mortality and morbidity.

Patients suffering from chronic renal (kidney) failure almost universally suffer loss of skeletal bone mass, termed renal osteodystrophy. While it is known that kidney malfunction causes a calcium and phosphate imbalance in the blood, to date replenishment of calcium and phosphate by dialysis does not significantly inhibit osteodystrophy in patients suffering from chronic renal failure. In adults, osteodystrophic symptoms often are a significant cause of morbidity. In children, renal failure often results in a failure to grow, due to the failure to maintain and/or to increase bone mass.

Osteoplasia, also known as osteomalacia ("soft bones"), is a defect in bone mineralization (e.g., incomplete mineralization), and classically is related to vitamin D deficiency (1,25-dihydroxy vitamin D3). The defect can cause compression fractures in bone, and a decrease in bone mass, as well as extended zones of hypertrophy and proliferative cartilage in place of bone tissue. The deficiency may result from a nutritional deficiency (e.g., rickets in children), malabsorption of vitamin D or calcium, and/or impaired metabolism of the vitamin.

Hyperparathyroidism (overproduction of the parathyroid hormone) is known to cause malabsorption of calcium, leading to abnormal bone loss. In children, hyperparathyroidism can inhibit growth, in adults the skeleton integrity is compromised and fracture of the ribs and vertebrae are characteristic. The parathyroid hormone imbalance typically may result from thyroid adenomas or gland hyperplasia, or may result from prolonged pharmacological use of a steroid. Secondary hyperparathyroidism also may result from renal osteodystrophy. In the early stages of the disease, osteoclasts are stimulated to resorb bone in response to the excess hormone present. As the disease progresses, the trabecular bone ultimately is resorbed and marrow is replaced with fibrosis, macrophages and areas of hemorrhage as a consequence of microfractures, a condition is referred to clinically as osteitis fibrosa.

Paget's disease (osteitis deformans) is a disorder currently thought to have a viral etiology and is characterized by excessive bone resorption at localized sites which flare and heal but which ultimately are chronic and progressive, and may lead to malignant transformation. The disease typically affects adults over the age of 25.

Although osteoporosis has been defined as an increase in the risk of fracture due to decreased bone mass, none of the presently available treatments for skeletal disorders can substantially increase the bone density of adults. A strong perception exists among physicians that drugs are needed which could increase bone density in adults, particularly in the bones of the wrist, spinal column and hip that are at risk in osteopenia and osteoporosis.

Current strategies for the prevention of osteoporosis may offer some benefit to individuals but cannot ensure resolution of the disease. These strategies include moderating physical activity, particularly in weight-bearing activities, with the onset of advanced age, including adequate calcium in the diet, and avoiding consumption of products containing alcohol or tobacco. For patients presenting with clinical osteopenia or osteoporosis, all current therapeutic drugs and strategies are directed to reducing further loss of bone mass by inhibiting the process of bone absorption, a natural component of the bone remodeling process that occurs constitutively.

For example, estrogen is now being prescribed to retard bone loss. There is, however, some controversy over whether there is any long term benefit to patients and whether there is any effect at all on patients over 75 years old. Moreover, use of estrogen is believed to increase the risk of breast and endometrial cancer. High doses of dietary calcium with or without vitamin D have also been suggested for postmenopausal women. However, ingestion of high doses of calcium can often have unpleasant gastrointestinal side effects, and serum and urinary calcium levels must be continuously monitored.

Other therapeutics which have been suggested include calcitonin, bisphosphonates, anabolic steroids and sodium fluoride. Such therapeutics however, have undesirable side effects, for example, calcitonin and steroids may cause nausea and provoke an immune reaction, bisphosphonates and sodium fluoride may inhibit repair of fractures, even though bone density increases modestly, which that may prevent their usage.

The above disorders are examples of conditions that may lead to bone fractures, fissures or splintering of the bones in the individuals who suffer from a given disorder. Current therapeutic methods are insufficient to treat the disorders leaving a need for improved treatments of bone fractures when they occur in the individual. The present invention provides improved compositions, products and methods for locally treating bone fractures, fissures, splintering and similar breakages of the bone, or by strengthening decomposed bone tissue by increasing the mechanism of mineralization of the bone. It is conceivable that the current invention also causes mineralization of the surrounding connective tissue, such as collagen, cartilage, tendons, ligaments and other dense connective tissue and reticular fibers.

The Oral Cavity

With respect to tissue decomposition in the oral cavity, it is commonly known in the dental art that certain kinds of tooth decomposition and decay that occurs over time in the mouth is initiated by acid etching of the tooth enamel with the source of the acid being a metabolite resulting from bacterial and enzymatic action on food particles in the oral cavity. It is generally understood that plaque, a soft accumulation on the tooth surface consisting of an organized structure of microorganisms, proteinaceous and carbohydrate substances, epithelial cells, and food debris, is a contributory factor in the development of various pathological conditions of the teeth and soft tissue of the oral cavity. The saccharolytic organisms of the oral cavity which are associated with the plaque, cause a demineralization or decalcification of the tooth beneath the plaque matrix through metabolic activity which results in the accumulation and localized concentration of organic acids. The etching and demineralization of the enamel may continue until they cause the formation of dental caries and periodontal disease within the oral cavity.

Teeth are cycled through periods of mineral loss and repair also as a result of pH fluctuations in the oral cavity. The overall loss or gain of mineral at a given tooth location determine whether the carious process will regress, stabilize or advance to an irreversible state. Numerous interrelated patient factors affect the balance between the remineralization and demineralization portions of this cycle and include oral hygiene, diet, and the quantity and quality of saliva. At the most extreme point in this process, a restoration will be required to repair the tooth.

Methods for the prevention and reduction of plaque and tooth decay within the oral cavity commonly involve the brushing of the teeth using toothpastes; mechanical removal of the plaque with dental floss; administration and rinsing of the oral cavity with mouthwashes, dentifrices, and antiseptics; remineralization and whitening of the teeth with fluoride agents, calcium agents and whitening agents, and various other applications to the oral cavity. Still missing in the field is a delivery system for the remineralization of teeth that would address the challenges of demineralization facing the teeth continually in the oral cavity.

A tooth that has reached an advanced stage of decay often requires installation of a dental restoration within the mouth. Half of all dental restorations fail within 10 years, and replacing them consumes 60% of the average dentist's practice time. Current dental materials are challenged by the harsh mechanical and chemical environment of the oral cavity with secondary decay being the major cause of failure. Development of stronger and longer-lasting biocompatible dental restorations by engineering novel dental materials or new resin systems, enhancing existing materials, and incorporating bioactive agents in materials to combat microbial destruction and to sustain the harsh mechanical and chemical environment of the oral cavity continues to be desired.

Despite numerous preventive oral health strategies, dental caries remains a significant oral health problem. More than 50% of children aged 6-8 will have dental caries and over 80% of adolescents over age 17 will have experienced the disease. Caries is also seen in adults both as a primary disease and as recurrent disease in already treated teeth. Advances in diagnosis and treatment have led to non-invasive remineralizing techniques to treat caries. However mechanical removal of diseased hard tissue and restoration and replacement of enamel and dentin is still the most widely employed clinical strategy for treating primary caries, restoring function to the tooth and also blocking further decay. In addition, nearly 50% of newly placed restorations are replacement of failed restorations. Clearly, restorative materials are a key component of treating this widespread disease.

The selection of a restorative material has significantly changed in recent years. While dental amalgam is still considered a cost effective material, there is a growing demand for tooth colored alternatives that will provide the same clinical longevity that is enjoyed by dental amalgam. The use of composite resins has grown significantly internationally as a material of choice for replacing amalgam as a restorative material for posterior restorations. This demand is partially consumer driven by preference for esthetic materials and the concerns regarding the mercury content of amalgam. It is also driven by dentists recognizing the promise of resin-based bonded materials in preserving and even supporting tooth structure. Numerous studies have suggested that bonding the restoration to the remaining tooth structure decreases fracture of multi-surface permanent molar preparations. Unfortunately, posterior teeth restored with direct resin restorative materials have a higher incidence of secondary caries. This has led to shorter clinical service and narrower clinical indications for composite resin materials compared to amalgam.

The most frequently cited reason for restoration replacement is recurrent decay around or adjacent to an existing restoration. It is likely that fracture at the margin due to polymerization shrinkage can lead to a clinical environment at the interface between a restoration and the tooth that collects dental plaque and thus promotes decay. Therefore, developing dental materials with anti-caries capability is a very high priority for extending the longevity of restorations.

Tooth Remineralization

Although natural remineralization is always taking place in the oral cavity, the level of activity varies according to conditions in the mouth as discussed. Incorporation of fluoride during the remineralization process has been a keystone for caries prevention. The effectiveness of fluoride release from various delivery platforms, including certain dental restorative materials has been widely demonstrated. It is commonly accepted that caries prevention from fluoride is derived from its incorporation as fluorapatite or fluoride enriched hydroxyapatite in the tooth mineral thereby decreasing the solubility of tooth enamel. More recently, anti-caries activity has been demonstrated using the strategy of increasing solution calcium and phosphate concentrations to levels that exceed the ambient concentration in oral fluids. In order for fluoride to be effective at remineralizing previously demineralized enamel, a sufficient amount of calcium and phosphate ions must be available. For every two (2) fluoride ions, ten (10) calcium ions and six (6) phosphate ions are required to form a cell of fluorapatite ($Ca10(PO4)6F2$). Thus the limiting factor for net enamel remineralization is the availability of calcium and fluoride in saliva.

The low solubility of calcium phosphates has limited their use in clinical delivery platforms, especially when in the presence of fluoride ions. These insoluble phosphates can only produce available ions for diffusion into the enamel in an acidic environment. They do not effectively localize to the tooth surface and are difficult to apply in clinically usable forms. Because of their intrinsic solubility, soluble calcium and phosphate ions can only be used at very low concentrations. Thus they do not produce concentration gradients that drive diffusion into the subsurface enamel of the tooth. The solubility challenge is exacerbated by the even lower solubility of calcium fluoride phosphates.

Several commercially available approaches exist using calcium and phosphate preparations that have been commercialized into various dental delivery models. These have been reportedly compounded to overcome the limited bioavailability of calcium and phosphate ions for the remineralization process. The first technology uses casein phosphopeptide (CCP) stabilized with amorphous calcium phosphate (ACP) (RECALDENT® CCP-ACP of Cadbury Enterprises Pte. Ltd.). It is hypothesized that the casein phosphopeptide can facilitate the stabilization of high concentrations of ionically available calcium and phosphate even in the presence of fluoride. This formulation binds to pellicle and plaque and while the casein phosphopeptide prevents the formation of dental calculus, the ions are available to diffuse down the concentration gradient to subsurface enamel lesions facilitating remineralization. As compared to the CCP-ACP, in the composition of the invention, biologically available ions are available due to the fact that the salts are already solvated in the microcapsule of the invention. Amorphous calcium phosphate is not soluble in water or saliva. Although the manufacturer claims release of bioavailable ions from amorphous calcium phosphate, it is not as a result of the dissolution of the complex. A second technology (ENAMELON®) uses unstabilized amorphous calcium phosphate. Calcium ions and phosphate ions are introduced as a dentifrice separately in a dual chamber device forming amorphous calcium phosphate in-situ. It is proposed that formation of the amorphous complex promotes remineralization. A third approach uses a so-called bioactive glass (NOVAMIN® of NovaMin Technology Inc.) containing calcium sodium phosphosilicate. It is proposed that the glass releases calcium and phosphate ions that are available to promote remineralization. More recently dental composite formulations have been compounded using zirconia-hybridized ACP that may have the potential for facilitating clinical remineralization.

While the Recaldent® and Enamelon® preparations have both in-situ and in-vivo evidence suggesting enhanced remineralization, these are topically applied and do not specifically target the most at risk location for recurrent caries at the tooth restoration interface. While the bioactive glass and the zirconia-hybridized-ACP filler technologies have potential, they are relatively inflexible in terms of the range of formulations in which they might be used due to the challenges of dealing with brittle fillers and some of the limitations on controlling filler particle size.

Another approach taken to decrease caries in the oral cavity is the limiting of demineralization of enamel and bone by drinking water fluoridation. It has been shown that the fluoride contained in drinking water incorporates to some extent into hydroxyapatite, the major inorganic component of enamel and bone. Fluoridated hydroxyapatite is less susceptible to demineralization by acids and is thus seen to resist the degradation forces of acidic plaque and pocket metabolites. In addition, fluoride ion concentration in saliva is increased through consumption of fluoridated drinking water. Saliva thus serves as an additional fluoride ion reservoir and in combination with buffering salts naturally found in salivary fluid, fluoride ions are actively exchanged on the enamel surface, further offsetting the effects of demineralizing acid metabolites.

Notwithstanding the established benefits of fluoride treatment of teeth, fluoride ion treatment can result in irregular spotting or blotching of the teeth depending on the individual, whether administered through drinking water or by topically applied fluoride treatment. This effect is known to be both concentration related and patient specific. In addition, the toxicology of fluoride is being studied as to its long term effect on human health. Desired is a targeted approach of fluoridation in the oral cavity.

Another approach to limiting the proliferation of microflora in the oral environment is through topical or systematic application of broad-spectrum antibacterial compounds. Reducing the number of oral microflora in the mouth results in a direct reduction or elimination of plaque and pocket accumulation together with their damaging acidic metabolite production. The major drawback to this particular approach is that a wide variety of benign or beneficial strains of bacteria are found in the oral environment which may be killed by the same antibacterial compounds in the same manner as the harmful strains. In addition, treatment with antibacterial compounds may select for certain bacterial and fungi, which may then become resistant to the antibacterial compound administered and thus proliferate, unrestrained by the symbiotic forces of a properly balanced microflora population. Thus the application or administration of broad-spectrum antibiotics alone is ill-advised for the treatment of caries and a more specific, targeted approach is desired.

Tooth Whitening

Cosmetic dental whitening or bleaching has become extremely desirable to the general public. Many individuals desire a "bright" smile and white teeth, and consider dull and stained teeth cosmetically unattractive. Unfortunately, without preventive or remedial measures, stained teeth are almost inevitable due to the absorbent nature of dental material. Everyday activities such as eating, chewing, or drinking certain foods and beverages (in particular coffee, tea, and red wine) and smoking or other oral use of tobacco products cause undesirable staining of surfaces of teeth. Extrinsic staining of the acquired pellicle arises as a result of compounds such as tannins and polyphenolic compounds which become trapped in and tightly bound to the proteinaceous layer on the surfaces of teeth. This type of staining can usually be removed by mechanical methods of tooth cleaning. In contrast, intrinsic staining occurs when staining compounds penetrate the enamel and even the dentin or arise from sources within the tooth. The chromogens or color causing substances in these materials become part of the pellicle layer and can permeate the enamel layer. Even with regular brushing and flossing, years of chromogen accumulation can impart noticeable tooth discoloration. Intrinsic staining can also result from microbial activity, including that associated with dental plaque. This type of staining is not amenable to mechanical methods of tooth cleaning and chemical methods are required.

Without specifically defining the mechanism of action of the present invention, the compositions, products and methods of the present invention enable the precipitation of salts onto the surfaces of the teeth in the oral cavity and make the salts available for adherence to the tooth surface and remineralization of the teeth. The mineralizing salts are deposited in the interstitial spaces of the teeth, making the teeth smoother, increasing the reflection of light from the surface of the teeth and thereby giving the teeth a brighter, more lustrous appearance and whiter visual effect. Furthermore, the remineralization process provides for improved enamel remineralization thus treating and preventing caries in the oral cavity.

Accordingly, there is need for improved compositions, methods and products that overcome the limitations of the prior art. The challenge remains to create microcapsules and microcapsule formulations that enhance the mechanical properties of the composite and wherein the liquid phases within the semi-permeable microcapsules provide beneficial materials to the composite or surface to which the composite is attached. Such material, therefore, include materials for use in a tooth remineralization technology platform for incorporating stable and effective tissue remineralization ions that can be incorporated into a myriad of dental materials and variety of products. Such a delivery platform would facilitate the formulation of dental products such as any number of dentifrices capable of remineralization of the teeth.

The embodiments of the compositions, products and methods, as described herein, satisfy these and other needs. For purposes of use with a tooth material, the ultimate impact is an improved microcapsule having a reduction in recurrent caries, the most prevalent reason for restoration replacement; whitening of the teeth; and resulting improvement in overall strength and health of the teeth in the oral cavity.

SUMMARY OF THE INVENTION

Compositions, methods, and products that benefit from improved mechanical properties related to better homogenization of the continuous and discontinuous phase of a composite, by functionalizing the surface of a microcapsule which can then covalently bond with other structures.

Another aspect of the present invention provides compositions, products and methods that use microcapsules comprising a polymerizable functional group therein to enhance the material properties of the composite, wherein the microcapsules can be filled with any number of biologic, mechanical, restorative, or other materials which are suitable for treating the materials which the composite is attached to. For example, remineralization materials may include salt ions, which serve to increase bone mineralization at localized sites or remineralization of teeth directly in the oral cavity. Such materials, thus, may be utilized in conjunction with treatments of a wide variety of conditions where it is desired to increase bone or tissue mass as a result of any condition which can be improved by bioavailability of physiological salts, particularly of calcium and phosphate.

Another aspect of this invention relates to further improvement of mechanical properties of a composite by the ability to create novel fillers with unique morphologies and chemical compositions. Accordingly, embodiments as described herein relate to the simplification of a manufacturing process that eliminates the need for additional steps for the surface treatment of fillers. Accordingly, the embodiments provide for improvements of the mechanical properties of the composite and it does so in a way that the filler can be made to carry therapeutic agents that can be released in a controllable manner.

In further embodiments, disclosed are compositions and methods that improve the mechanical properties of a composite or improve the manufacturing process of fillers used in composites by use of non-therapeutic fillers. The present invention provides products that are useful in a number of industries, especially for oral health care. The present invention provides compositions that include fillers disposed of within the discontinuous phase, wherein a particular filler includes liquid filled microcapsules that are surface functionalized with a polymerizable functional group. These fillers, when combined with monomers and an initiator allow for the generation of a composite that has the continuous and discontinuous phases covalently bonded together. The covalent bonding of the continuous and discontinuous phases leads to a significant improvement in mechanical properties of a composite, especially in the area of fracture mechanics. The composition of this invention affords for the opportunity of producing bondable bioactive microcapsules where the microcapsule is filled with a liquid that contains a therapeutic agent. The composition of this invention not only provides superior fracture properties by nature of the covalent bonding between the filler and continuous phase, but it can provide for improvement of other mechanical properties if the microcapsule is filled with energy absorbing materials such as rubbers or silicones.

Another aspect of the disclosure includes bondable bioactive microcapsules suitable for industrial products in the dental materials industry, wherein liquid encapsulated in the bondable microcapsule contained aqueous salt solutions of a calcium, phosphate or fluoride containing salt, then incorporation of those microcapsules in a dental materials product for promoting remineralization. Furthermore, the liquid encapsulated in the bondable microcapsule contained aqueous solutions of an antimicrobial agent, including, but not limited to benzalkonium chloride or cetylpyridinium chloride then incorporation of those microcapsules into a dental materials product with antimicrobial properties would be achieved. Similarly, combinations of remineralizing and antimicrobial compounds are desirable in certain embodiments.

In essence, this invention simultaneously enhances the mechanical properties and simplifies the manufacturing of a composite by virtue of having built-in surface functionalization, while adding the benefit of having the filler be therapeutic or mechanically toughening depending on its chemical composition.

Another aspect of the disclosure includes a composition comprising of a monomer, an initiator, and a microcapsule encapsulating an aqueous solution of a salt, wherein said microcapsule has a surface functionalized with a polymerizable functional group capable of polymerizing with said monomer.

Another aspect of the disclosure includes a composition comprising of a monomer, an initiator, and a microcapsule encapsulating an aqueous solution of a salt, specifically calcium, fluoride or phosphate or combinations thereof, wherein said microcapsule has a surface functionalized with a polymerizable functional group capable of polymerizing with said monomer.

Another aspect of the disclosure includes a composition comprising of a polymeric continuous phase and a microcapsule encapsulating an aqueous solution of a salt, specifically calcium, fluoride or phosphate or combinations thereof, wherein said microcapsule has a surface functionalized with a polymerizable functional group capable of polymerizing with said monomer.

Another aspect of the disclosure includes a composition comprising of a polymeric continuous phase and a microcapsule encapsulating a fluid, wherein said microcapsule has a surface functionalized with a polymerizable functional group that is covalently bonded to the continuous phase.

A further embodiment is directed to a composition comprising a continuous phase comprising a monomer, and a discontinuous phase comprising at least one filler comprising a microcapsule encapsulating a fluid, and an initiator, wherein said microcapsule has a surface functionalized with a polymerizable functional group capable of polymerizing with said monomer.

A further embodiment is directed to a composition comprising of a monomer, an initiator, and a microcapsule encapsulating an aqueous solution of a salt selected from the group consisting of: benzalkonium, cetylpyridinium, and iodide, and combinations thereof, wherein said microcapsule has a surface functionalized with a polymerizable functional group capable of polymerizing with said monomer.

A further embodiment is directed to a composition comprising of a TEGMA and bisGMA monomers, an initiator, and a microcapsule encapsulating an aqueous solution of a salt selected from the group consisting of: benzalkonium, cetylpyridinium, and iodide, and combinations thereof, wherein said microcapsule has a surface functionalized with a polymerizable functional group capable of polymerizing with said monomer. The microcapsule is between 2-5 w/w % of the composition and has methacrylate functional groups on the surface, wherein the methacrylate group reacts with the methacrylate groups of the monomers in the continuous phase.

Another aspect of the disclosure provides a method for manufacturing a composition having a microcapsule and a continuous phase, wherein said microcapsule comprises a functionalized surface capable of covalently bonding to the continuous phase comprising: mixing an oligomeric urethane by reaction of a diol and diisocyanate, in which the diisocyanate is used in molar excess, and reacting for a about 1 hour; adding 2-hydroxyethylmethacrylate to the resulting oligomeric urethane mixture to terminate chain ends with methacrylate functional groups; isolating the functionalized urethane; adding the isolated functionalized urethane to an oil phase comprising an emulsifying agent and an organic solvent wherein a surfactant free inverse emulsion is formed with the addition of an aqueous phase that may contain a salt; adding diol to the surfactant free reverse emulsion to polymerize the urethane oligomers and encapsulate the aqueous solution; and isolating the microcapsules by centrifugation.

Another aspect of the disclosure provides a method for manufacturing a composition having a microcapsule and a continuous phase, wherein said microcapsule comprises a functionalized surface capable of covalently bonding to the continuous phase comprising: synthesizing oligomeric or polymeric material with functional groups capable of reacting with monomers of a continuous phase; isolating the functionalized oligomeric or polymeric material; adding the isolated functionalized material to an oil phase comprising an emulsifying agent and an organic solvent wherein a surfactant free inverse emulsion is formed with the addition of an aqueous phase that may contain a salt; adding chain extender to the surfactant free reverse emulsion to increase the molecular weight of the functionalized oligomeric or polymeric material and encapsulate the aqueous solution; and isolating the functionalized microcapsules by centrifugation.

Another aspect of the invention is a method of use any one of the compositions to impart additional structural features into a polymer or composite material.

BRIEF DESCRIPTION OF THE DRAWINGS

FIG. 1 is a drawing of a flow-chart showing the preparation of an embodiment of a surface functionalized microcapsule.

DETAILED DESCRIPTION OF THE INVENTION

Figure 2:
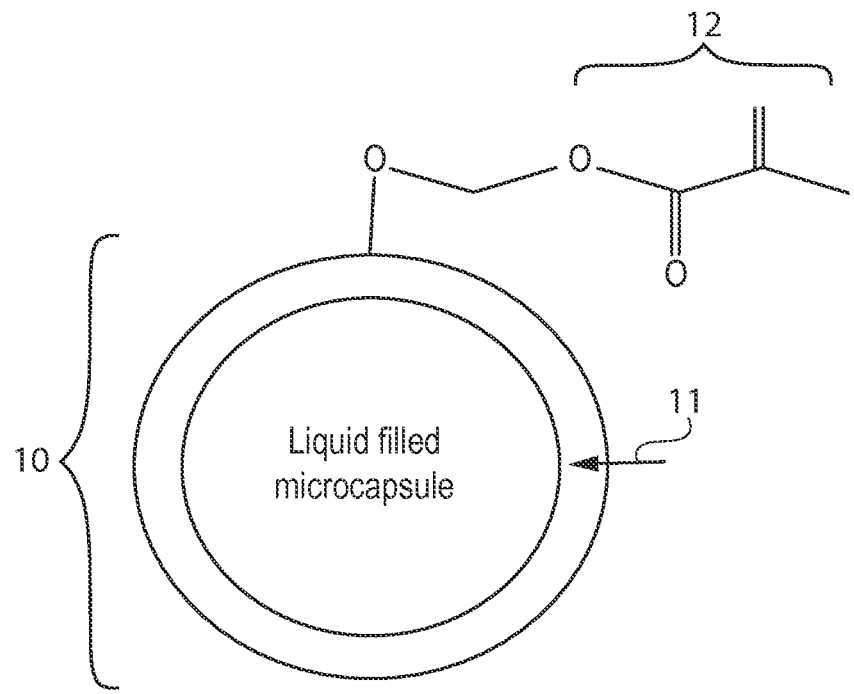
FIG. 2 depicts a liquid filled microcapsule having a polymer exterior and a liquid center, which is in contact with the polymer and attached a functional group.

The embodiments of the invention and the various features and advantages thereto are more fully explained with references to the non-limiting embodiments and examples that are described and set forth in the following descriptions of those examples. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the claims.

As used herein, terms such as "a," "an," and "the" include singular and plural referents unless the context clearly demands otherwise.

As used herein, the term "about" means within 10% of a stated number.

There exists a broad need for improved microcapsule compositions and methods useful for therapeutic agent delivery. In particular, there is a need for an improved microcapsule-based technology for delivering therapeutic agents to diverse tissue types in a stable and time-controlled manner.

Microcapsules have other uses in far ranging fields based on the chemical structure and properties of the microcapsules. For example, it may be advantageous to use microcapsules and compositions comprising such microcapsules with plastics, gels, pastes, adhesives, paint products, and generally with products that utilize polymers of any sort. Indeed, such improvements may lead to uses in industries unrelated to health and oral health such as in manufacturing, aeronautics, plastic manufacturing, and similar fields.

One aspect of this invention addresses the challenge of incorporating fillers into continuous phases. Compositions, methods and products that benefit from improved mechanical properties related to better homogenization of the continuous and discontinuous phase of a composite is addressed in this invention. Another aspect of this invention relates to further improvement of mechanical properties of a composite by the ability to create novel fillers with unique morphologies and chemical compositions. This invention relates to the simplification of a manufacturing process that eliminates the need for additional steps for the surface treatment of fillers. This invention not only improves the mechanical properties of the composite, it does so in a way that the filler can be made to carry therapeutic agents that can be released in a controllable manner.

Composites are ubiquitous in structural materials. Typically a polymeric continuous phase is mixed with discontinuous filler or fillers. The mixing of the filler into the continuous phase is done with the purpose of enhancing some property of the composite that could otherwise not be achieved by the continuous phase alone. A significant challenge that remains in the development of composite materials is the discontinuity that is created between the continuous phase and the filler. This discontinuity provides a pathway for crack propagation through the composite that results in mechanical properties that are not optimal, and at times prohibitive of using a particular continuous/filler combination that would otherwise have been suitable for a target application.

In order to address the mechanical issues created by the introduction of the filler into the continuous phase, additional manufacturing steps are typically required. For example, in the field of dental materials, a variety of glass fillers are used to improve the performance of the composite. However, the glass fillers, if used untreated, provide a facile pathway for crack propagation in the material. In order to address this issue, glass fillers are subjected to an additional manufacturing step. Prior to inclusion into a dental formulation, the glass fillers are silanated. The silanation process provides a surface treatment that allows the glass filler to form a covalent bond to the continuous phase. The covalent linkage between the filler and the continuous phase eliminates the facile pathway for crack propagation. In order for the crack to propagate through the composite with the surface treated filler, significantly more energy is required, thereby enhancing the fracture mechanics of the composite (e.g. fracture toughness is increased).

Other examples of surface treatment exist to create a better bonding surface in composites. One such example is corona, or plasma treatment. Many plastics, such as polyethylene and polypropylene, have chemically inert and non-porous surfaces with low surface tensions causing them to be non-receptive to bonding with printing inks, coatings, and adhesives. Although results are invisible to the naked eye, surface treating modifies surfaces to improve adhesion. However, due to the non-covalent nature of the surface treatment, plasma treatment typically becomes less effective over time.

The present application provides for improved or simplified manufacturing methods of organic or hybrid based fillers used in composite materials. The method of microcapsule synthesis eliminates the need for additional manufacturing steps typically required for the effective incorporation of discontinuous fillers into composite materials. Many composite based products are envisioned from this invention, including composite based formulations of sealants, cements, glazes, varnishes and many other dental and non-dental based materials.

Compositions, methods and products that benefit from improved mechanical properties related to better homogenization of the continuous and discontinuous phase of a composite. This is achieved by functionalizing the exterior surface of microcapsules such that the microcapsules can covalently bond with the continuous phase. Accordingly, the continuous phase and the discontinuous phase are covalently bonded upon initiation or reaction of the materials. This approach can generally be accomplished by preparing microcapsules that have a polymeric shell. This polymeric shell can be synthesized with functional groups off the back bone or side chain of the polymer that can subsequently undergo chemical reactions with other functional groups present in the monomer or polymer of a continuous phase resulting in a bond between the microcapsule and the continuous phase.

Accordingly, the present disclosure describes improvements in microcapsules, their formulation, and compositions, compounds, and methods for the mineralization of various physiological tissues, including mineralized connective tissues, primarily of bone and teeth using such microcapsules. Mineralized connective tissue or tissues include teeth, bone, and various connective tissues such as collagen, cartilage, tendons, ligaments and other dense connective tissue and reticular fibers (that contains type III collagen) of a mammal, including a human being. For purposes of definition in this specification, "mineralized tissue" shall mean bone and teeth specifically. Each of the terms "mineralization" and "tissue mineralization" are used interchangeably herein and mean a process in which crystals of calcium phosphate are produced by bone-forming cells or tooth-forming cells and laid down in precise amounts within the fibrous matrix or scaffolding of the mineralized tissue as defined hereinabove.

Calcium phosphates are a class of minerals containing, but not limited to, calcium ions together with orthophosphates, metaphosphates and/or pyrophosphates that may or may not contain hydrogen or hydroxide ions.

For purposes of definition in this specification, "remineralization" is the process of restoring minerals, in the form of mineral ions, to the hydroxyapatite latticework structure of a tooth. As used herein, the term "remineralization" includes mineralization, calcification, re-calcification and fluoridation as well as other processes by which various particular ions are mineralized to the tooth. The term "teeth" or "tooth" as used herein includes the dentin, enamel, pulp and cementum of a tooth within the oral cavity of an animal, including a human being.

In certain embodiments, the present invention provides methods for remineralization surface of a tooth material by using the microcapsules formulations, as described herein, containing one or more materials disposed of therein which are suitable for being released from the microcapsule for remineralizing a tooth material or bone surface. For purposes of definition in this specification, as referred to herein, a "tooth material" refers to natural teeth, dentures, dental plates, fillings, caps, crowns, bridges, dental implants, and the like, and any other hard surfaced dental prosthesis either permanently or temporarily fixed to a tooth within the oral cavity of an animal, including a human being.

Another aspect of this invention relates to further improvement of mechanical properties of a composite by the ability to create novel fillers with unique morphologies and chemical compositions. Accordingly, this invention relates to the simplification of a manufacturing process that eliminates the need for additional steps for the surface treatment of fillers. This invention not only improves the mechanical properties of the composite, it does so in a way that the filler can be made to carry therapeutic agents that can be released in a controllable manner.

The present invention presents compositions and methods that improve the mechanical properties of a composite or improve the manufacturing process of fillers used in composites. The present invention provides products that are useful in a number of industries, especially for oral health care. The present invention provides compositions that include fillers, especially liquid filled microcapsules that are surface functionalized with a polymerizable functional group. These fillers, when combined with monomers and an initiator allow for the generation of a composite that has the continuous and discontinuous phases covalently bonded together. The covalent bonding of the continuous and discontinuous phases leads to a significant improvement in mechanical properties of a composite, especially in the area of fracture mechanics.

The composition of this invention affords for the opportunity of producing bondable bioactive microcapsules if the filler is a microcapsule filled with a liquid that contains a therapeutic agent. The composition of this invention not only provides superior fracture properties by nature of the covalent bonding between the filler and continuous phase, but it can provide for improvement of other mechanical properties if the microcapsule is filled with energy absorbing materials such as rubbers or silicones. Indeed, several fillers can be utilized to produce a variety of microcapsules, which can then be combined together. In particular embodiments it is particularly suitable to mix one of more of a variety of microcapsules to provide a composition with certain physical and chemical properties, whereby the release of different materials from the different microcapsules provides advantageous effects. Accordingly, antimicrobial, remineralizing, and physical property enhancing microcapsules can be admixed alone, on in combinations thereof. Other suitable filler components include detergents, dyes, abrasives, flavors, and other components known to one of skill in the art that are suitable for filling in a microcapsule.

The bondable bioactive microcapsules are suitable for industrial products in the dental materials industry. If the liquid encapsulated in the bondable microcapsule contained aqueous salt solutions of a calcium, phosphate or fluoride containing salt, then incorporation of those microcapsules in a dental materials product for promoting remineralization would be desirable. If the liquid encapsulated in the bondable microcapsule contained aqueous solutions of an antimicrobial agent such as benzalkonium chloride or cetylpyridinium chloride then incorporation of those microcapsules into a dental materials product with antimicrobial properties would be achieved.

In essence, this invention simultaneously enhances the mechanical properties and simplifies the manufacturing of a composite by virtue of having built-in surface functionalization, while adding the benefit of having the filler be therapeutic or mechanically toughening depending on its chemical composition.

This results in a composition comprising of a continuous phase and a discontinuous phase, wherein in the continuous phase is provided a monomer and optionally an initiator, and the discontinuous phase a microcapsule encapsulating a material, for example, an aqueous solution of a salt, wherein said microcapsule has a surface functionalized with a polymerizable functional group capable of polymerizing with said monomer. Indeed, in particular embodiments, the salt is a calcium, fluoride, or phosphate salt, or combinations thereof. Other suitable salts may be preferred in non-dental treatments and are also suitable for use with the functionalized microcapsules described herein.

Similarly, the composition can be described as comprising a polymeric continuous phase, a microcapsule encapsulating a material, for example, an aqueous solution of a salt, specifically calcium, fluoride or phosphate or a combination thereof, wherein said microcapsule has a surface functionalized with a polymerizable functional group capable of polymerizing with said monomer.

Indeed, in particular embodiments, the composition comprises a polymeric continuous phase, a microcapsule encapsulating a fluid, wherein said microcapsule has a surface functionalized with a polymerizable functional group that is covalently bonded to the continuous phase.

A particularly suitable composition for pit and fissure sealant with remineralization capabilities and enhanced fracture toughness is described as follows. A pit and fissure sealant containing resin, glass fillers, microcapsules with acrylate functionalized surfaces that contain a 5 M aqueous solution of calcium nitrate, microcapsules with acrylate functionalized surfaces that contain a 6 M aqueous solution of potassium phosphate dibasic, and microcapsules with acrylate functionalized surfaces that contain an aqueous solution of sodium fluoride, and at least one photoinitiator.

Photoinitiators used in the compositions and materials described herein are additives that assist in the formation of polymers from the monomers. In many dental composite materials the photoinitiator is soluble in the continuous phase. Activation of the photoinitiator is performed by providing a light source, typically a high energy light source in the visible spectrum, which activates the initiator to initiate the polymerization process. However, suitable photoinitiators may also be in the discontinuous phase in the embodiments described herein. Other initiators may also be suitable based on the circumstances of use as is known to one of ordinary skill in the art.

In other compositions, a composition for pit and fissure sealant with antimicrobial properties and enhanced fracture toughness is described as follows. A pit and fissure sealant containing resin, glass fillers, microcapsules with acrylate functionalized surfaces that contain a 5 w/w % aqueous solution of benzalkonium chloride (5 w/w %), and photoinitiators (1 wt %).

In other compositions, a composite material with enhanced mechanical properties is described as follows. A resin mixture (16 wt % total) was first made by combining UDMA resin with TEGDMA resin in a 4/1 ratio. A photosensitizer (camphoroquinone) was added at 0.7 wt % of the total composition. An accelerator (ethyl-4-dimethylaminobenzoate) was added at 0.25 wt % of the total composition. An inhibitor (4-methoxyphenol) was added at 0.05 wt % of the total composition. The resin, photosensitizer, accelerator and inhibitor were combined in a flask and mixed at 50° C. Upon homogenization, the above resin blend was mixed with the following fillers (84 wt % total): silanated strontium glass 71 wt %, fumed silica 10 wt %, microcapsules with acrylate functionalized surfaces that contain high molecular weight silicone oil 3 wt %. Such composition can be used in any number of fields as described herein.

A method for the production of surface functionalized microcapsule filled with encapsulated aqueous remineralizing agents is described. An oligomeric urethane is synthesized by the reaction of a diol and a diisocyanate. The diisocyanate is used in a molar excess. After 1 hour of reaction between the diol and diisocyanate, oligomeric urethane is achieved. At this point 2-hydroxyethylmethacrylate is added to the synthesis medium of the urethane in order to terminate a percentage of the chain ends with methacrylate functional groups. The methacrylate functionalized urethane is isolated and added to an oil phase that contains an emulsifying agent. This solution is mixed and a surfactant free, inverse emulsion is formed as an aqueous solution containing sodium fluoride salt is added. After half an hour, diol is added to the surfactant free, inverse emulsion to effectively polymerize the urethane oligomers and encapsulate the aqueous solution. The microcapsules are isolated by centrifugation. The microcapsules have surface methacrylate functional groups that readily polymerize with other methacrylate monomers of a continuous phase.

In view of the polymers utilized, the microcapsules are non-biodegradable, and thus materials contained therein are released from the microcapsules via diffusion. This provides a different profile than biodegradable polymers or other polymers that are intended to burst, releasing the entire contents of the capsule at once.

In certain embodiments, the surface of the microcapsule is effectively functionalized with a vinyl group to allow the vinyl groups to covalently bond with the monomer in the continuous phase. The preparation of the vinyl group is performed through a three step process.

Figure 5:
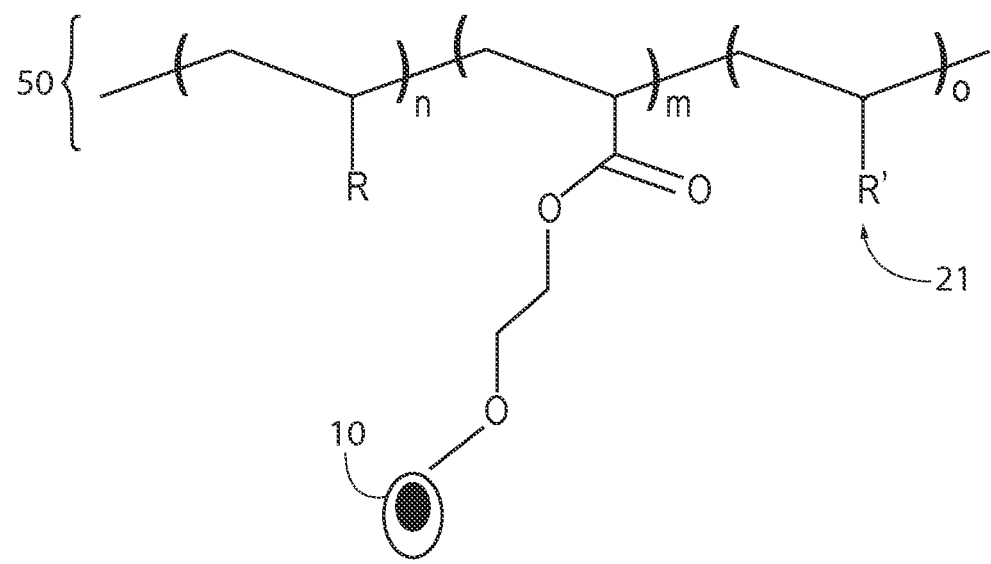
FIG. 5 depicts a bondable microcapsule wherein the functional group attached to the microcapsule is covalently bonded to a polymer.
Figure 6:
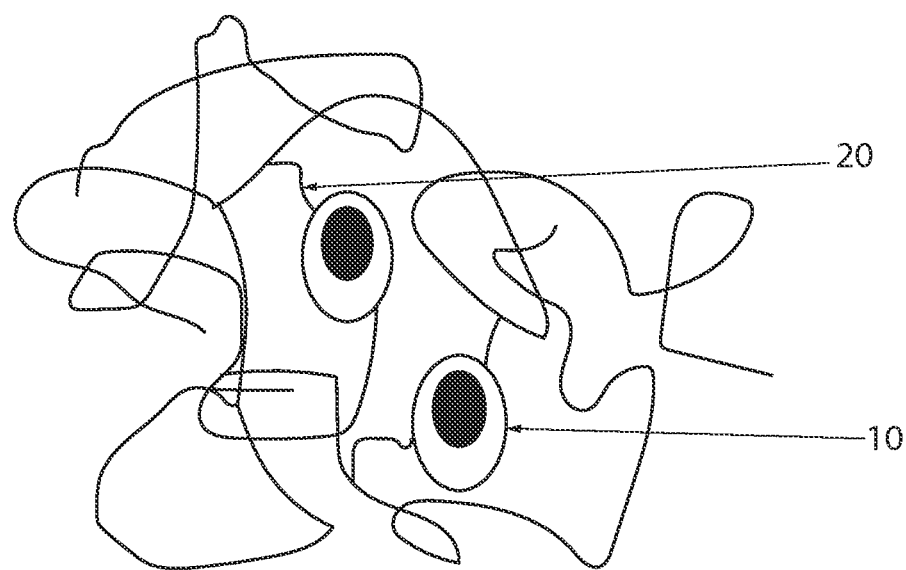
FIG. 6 depicts two microcapsules bonded to a now polymerized group of monomers.

Step 1: Preparation of Surface Functionalized Shell Material:

calcium ions, fluoride ions, phosphate ions, benzalkonium cations or cetyl pyridinium cations which can diffuse through the microcapsule membrane. Furthermore, through reaction of the methacrylate on the surface of the non-biodegradable microcapsule can then react with methacrylate in the continuous phase, which forms a carbon-carbon bond. The carbon-carbon covalent bond increases the fracture toughness of the composite material by bonding the microcapsule to the continuous phase, as depicted in FIGS. 5, 6, and 8B.

FIG. 1, provides a representative flow-chart for preparation of a surface functionalized shell material wherein the surface of such shell is functionalized to allow for covalent bonding between the microcapsule and the continuous phase. As described in Step 1, a chemical process results in vinyl terminated components functionalized to the shell of the microcapsule. Following in Step 2, the surface functionalized shell materials are combined with an emulsifying agent and an oil phase. The mixture is agitated with or without heat before an aqueous phase or other liquid phase, such as silicone, is added. An interfacial polymerization of the urethane in a surfactant free inverse emulsion. The surface functionalized microcapsules can then be isolated as appropriate.

In Step 3, the functionalized microcapsules are combined with the desired continuous phase monomers and initiators. The surface functional groups on the microcapsules are polymerizable with the monomer to create covalent bonds between the filler and the continuous phase. This provides that the functionalized microcapsules are then covalently bonded to the continuous phase.

Many classes of polymers can be utilized in the scope of the invention and the choice depends on the specific desired properties. Examples include, but are not limited to non-biodegradable iterations of the following classes: acrylic polymers, alkyd resins, aminoplasts, coumarone-indene resins, epoxy resins, fluoropolymers, phenolic resins, polyacetals, polyacetylenes, polyacrylics, polyalkylenes, polyalkenylenes, polyalkynylenes, polyamic acids, polyamides, polyamines, polyanhydrides, polyarylenealkenylenes, polyarylenealkylenes, polyarylenes, polyazomethines, poly-

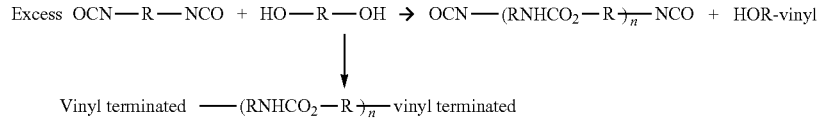

Step 2: Preparation of Surface Functionalized Microcapsule

Mix surface functionalized shell material, emulsifying agent, oil phase. Agitate mixture, with or without heat. Add an aqueous phase or other liquid phase (silicon). Perform an interfacial polymerization of the urethane in the surfactant free inverse emulsion. Isolate surface functionalized microcapsules.

Step 3: Formulation of Surface Functionalized Microcapsule

Combine surface functionalized microcapsule with desired continuous phase monomers and initiator. The surface functional group should be polymerizable with the monomer to create a covalent link between the filler and continuous phase.

In a preferred embodiment, a microcapsule is formed using polyurethane that has a fraction of the polyurethane methacrylate terminated. This forms a non-biodegradable capsule that is semi-permeable to therapeutic agents such as benzimidazoles, polybenzothiazoles, polybenzoxazinones, polybenzoxazoles, polybenzyls, polycarbodiimides, polycarbonates, polycarboranes, polycarbosilanes, polycyanurates, polydienes, polyester-polyurethanes, polyesters, polyetheretherketones, polyether-polyurethanes, polyethers, polyhydrazides, polyimidazoles, polyimides, polyimines, polyisocyanurates, polyketones, polyolefins, polyoxadiazoles, polyoxides, polyoxyalkylenes, polyoxyarylenes, polyoxymethylenes, polyoxyphenylenes, polyphenyls, polyphosphazenes, polypyrroles, polypyrrones, polyquinolines, polyquinoxalines, plysilanes, polysilazanes, polysiloxanes, polysilsesquioxanes, polysulfides, polysulfonamides, polysulfones, polythiazoles, polythioalkylenes, polythioarylenes, polythioethers, polythiomethylenes, polythiophenylenes, polyureas, polyurethanes, polyvinyl acetals, polyvinyl butyrals, polyvinyl formals. One skilled in the art will further appreciate that the selection of the specific type of polymer will impact the composition and permeability characteristics of the microcapsules of the invention and that certain polymers are more applicable to certain industrial applications as compared to applications in the field or dentistry.

In addition to the various possible polymers suitable for microcapsule formation, suitable polymerizable functional groups may also be used. Embodiments as disclosed herein utilize a bond between a functionalized microcapsule and a monomer. In preferred embodiments, a covalent bond is utilized, however, those of skill in the art will recognize than any number of suitable bonding mechanisms may be appropriate based on the chemistries utilized.

In preferred embodiments, the number of functional groups extending from a single microcapsule is between about 1% and 33% of all positions possible on the polyurethane microcapsule. However, further preferred embodiments include between about 0.1% and 99.9% of all possible positions, and preferably between about 1% and 50%, about 1% and 25%, about 1% and 10%, about 1% and 5%, and about 1% to about 3%.

The amount of functional groups can be modified as known to one of ordinary skill in the art, wherein the number of functional groups therefore can modify the properties of the ultimate polymer material formed through combination of the microcapsule and the monomers. In dental materials encapsulating calcium, fluoride, and phosphate, preferred amounts are between about 1% and 25%, and more preferably between about 1% and 5%.

Indeed, FIG. 2 provides a sample of a liquid filled microcapsule 10, having the liquid phase 11 in contact with the polymer shell, and the functional group 12 attached thereto.

Figure 3:
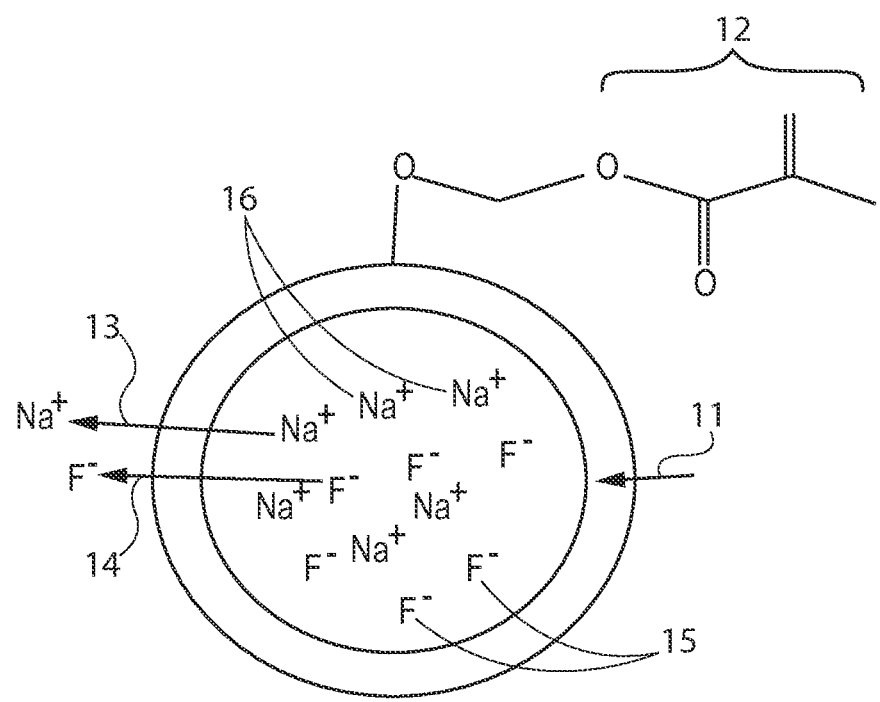
FIG. 3 depicts a liquid filled microcapsule and ions disposed of therein.

FIG. 3 provides further detail that representative ions, in this case Na+ 16 and F− 15 are each present in the liquid phase within the microcapsule. As is known to one of ordinary skill in the art, all anions (including fluoride) must have accompanying cations. The sodium and fluoride here are depicted ionically to depict that they are dissolved in water. Thereafter, through diffusion, the ions can exit the microcapsule, as depicted through lines 13 and 14.

The semi-permeable nature of the non-biodegradable polymer allows for diffusion of the materials contained therein. Diffusion rates can be modified based on several factors as known to one of ordinary skill in the art. The variables that control the diffusion rate include, but are not limited to the initial concentration of the ions in solution in the microcapsule, the chemical composition of the microcapsule, and the w/w loading of the microcapsules in the continuous phase.

Figure 4:
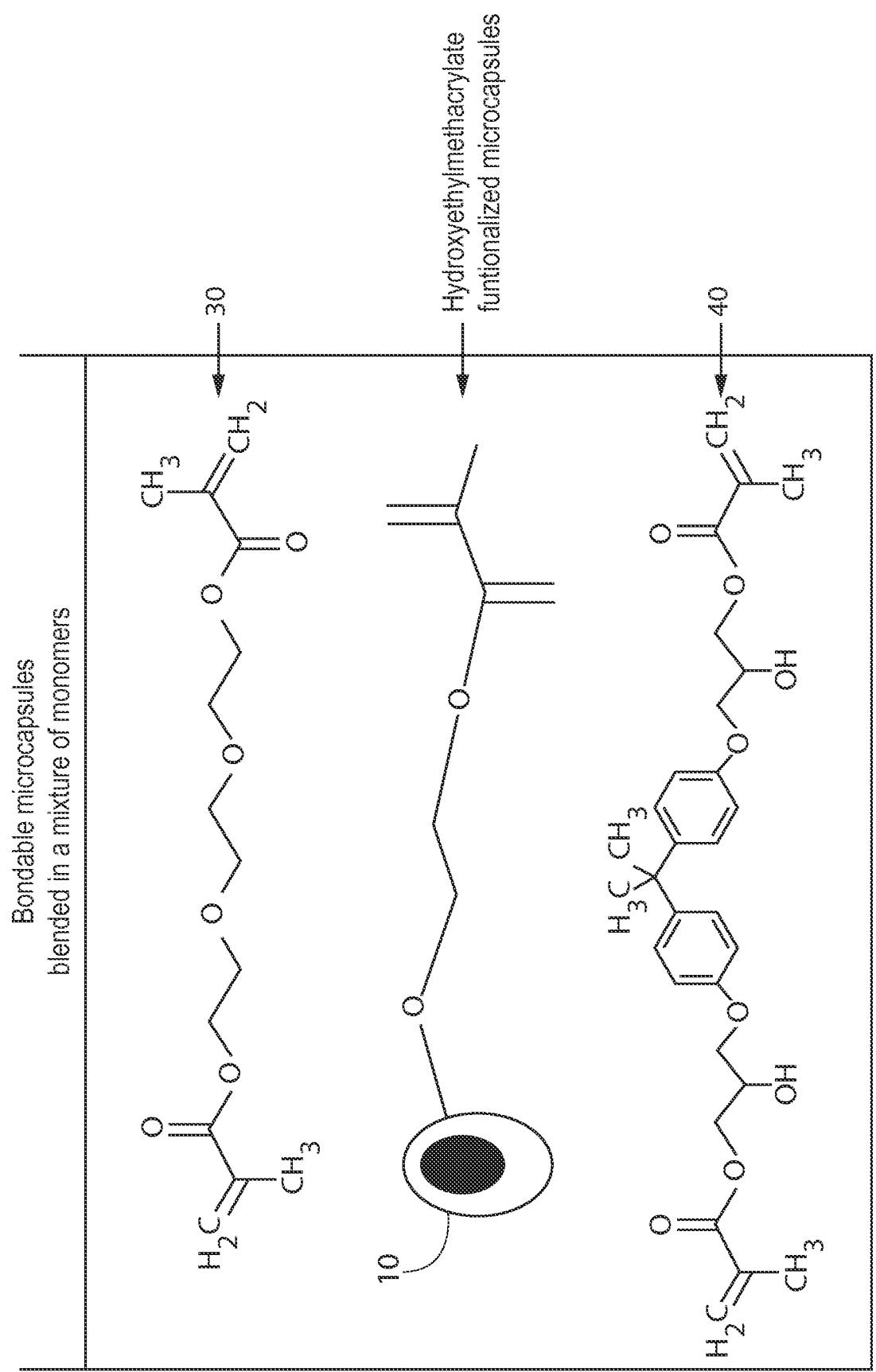
FIG. 4 depicts a bondable microcapsule positioned in a mixture of monomers, wherein two different monomers are depicted.

FIG. 4 provides a depiction of a bondable microcapsule which is a hydroxyethylmethacrylate functionalized microcapsule 10, which is positioned in a mixture of monomers, in this case, a first monomer triethylene glycol dimethacrylate 30 and a second monomer bisphenol A glycerolate dimethacrylate 40. These components can then react to allow the functional group on the microcapsule 10 to bond to the monomers 30 or 40 as depicted in FIG. 5, which shows a number of "m" microcapsules in the polymeric structure 50 dependent on how many repeat units are present.

Indeed, FIG. 5 is essentially a close-up of a microcapsule at the molecular level, whereas FIG. 6 provides an example of two microcapsules 10 bonded (whereas 20 is a bond between the polymer 50 and the microcapsule) within a polymer 50 at a macro level. In FIG. 5, R 22 and R' 21 can be a hydrogen or any functional group. Furthermore, the polymer 50 can include any number of n, m, and o repeating units. Indeed, in a composite material, once formed, the number of microcapsules within the material is solely dependent on the density and concentration of the microcapsules in the material. Ultimately, the surface functionalized microcapsule can be combined with the desired continuous phase monomers and initiator to react. The surface functional group should be polymerizable with the monomer to create a covalent bond between the filler (microcapsule) and the continuous phase monomer.

Figure 7:
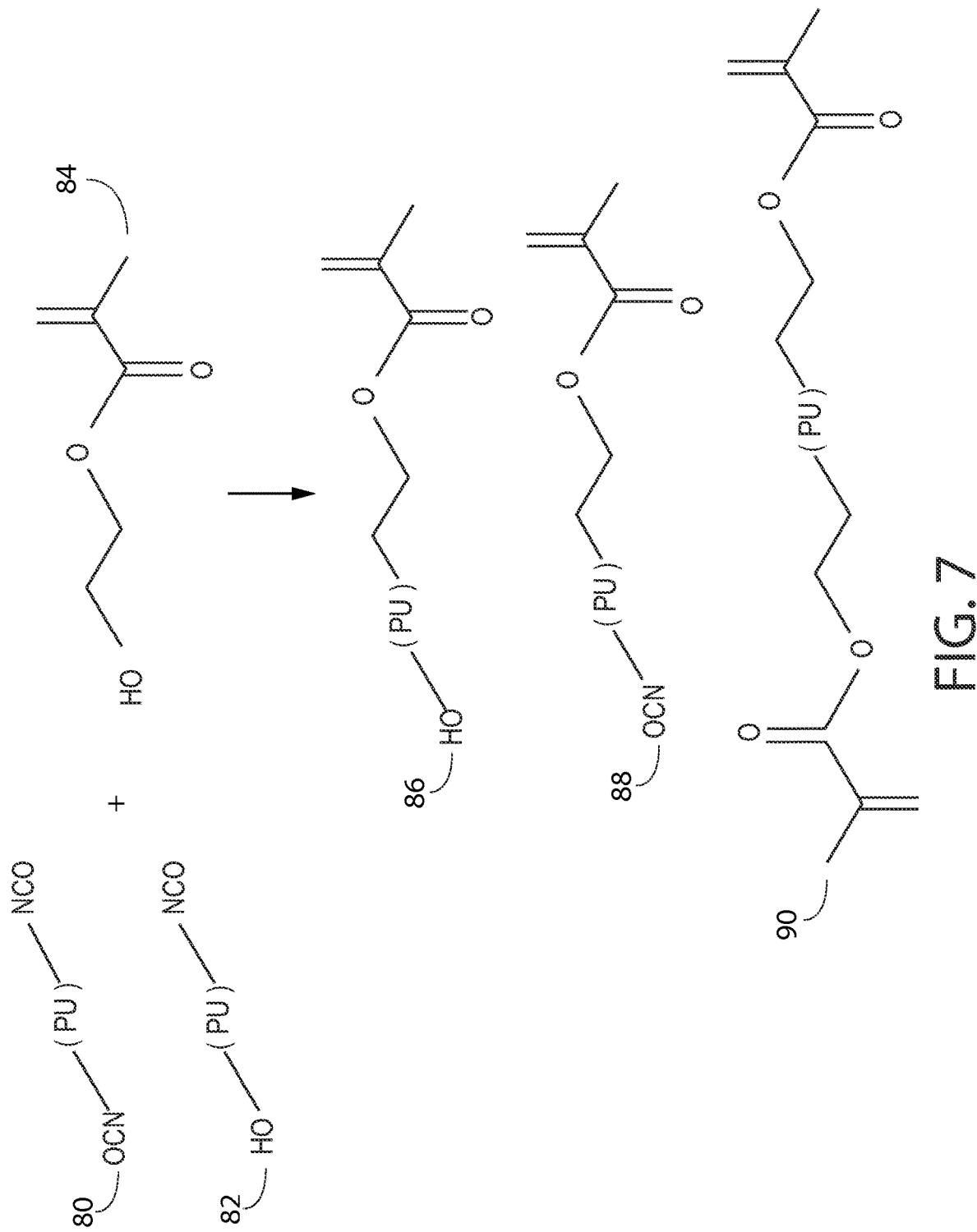
FIG. 7 depicts two possible urethane microcapsules having different functional groups that can react with HEMA to form several different functional microcapsules.

FIG. 7 depicts 2 possible chemical structures 80 and 82 of the shell materials end groups. In two of the potential structures, the shell material can have isocyanate functional groups capable of reacting with HEMA 84. This results in 3 potential shell materials with methacrylate end groups 86, 88 and 90. One structure can have a hydroxyl end group and a methacrylate end group, one structure can have an isocyanate end group and a methacrylate end group and one structure could have potentially two methacrylate end groups. Accordingly, these make a functionalized shell for the microcapsule 10 which can be bonded as depicted in FIG. 8.

Figure 8:
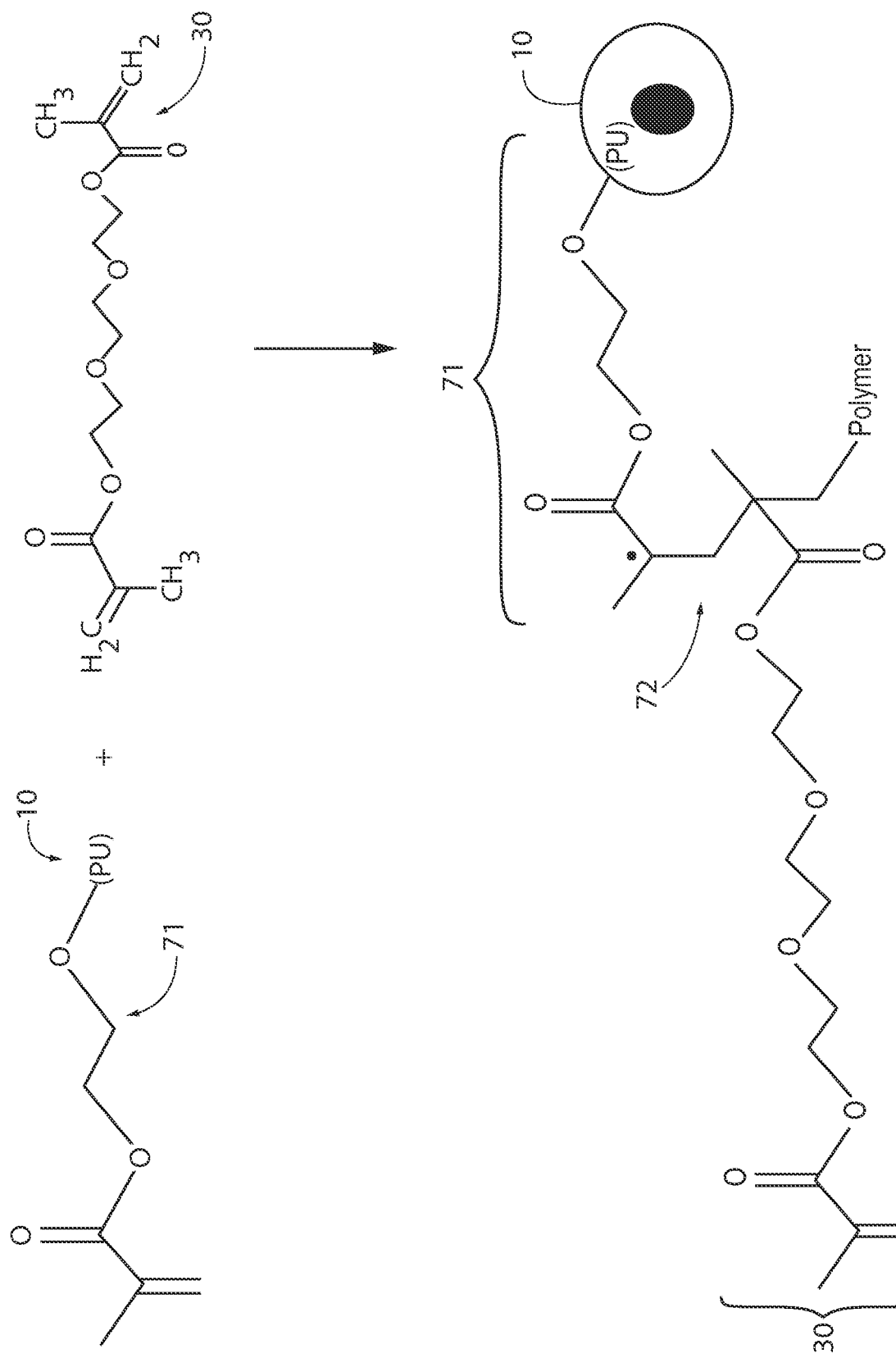
FIG. 8 depicts the methacrylate terminated polyurethane from FIG. 7 and a monomer which are then covalently bonded in the bottom structure.

FIG. 8 further depicts that the functionalized microcapsule 10 can then combine with a monomer 30. A polyurethane terminated with at least one methacrylate group 71 can react with a monomer such as triethylene glycol dimethacrylate 30 during a polymerization. In this reaction, the carbon-carbon pi bonds 72 add together in a series of addition reaction to generate a polymeric structure where the methacrylate group 71 is bonded to the monomer 30, thus binding the microcapsule 10 to the monomer. In FIG. 8 and as described herein, this can be accomplished by a radical reaction in which the methacrylate functional group of the microcapsule adds to a growing polymer chain or network.

In other embodiments, a composition having functionalized microcapsules is suitable for admixing into one of any known paint products. In the aspect of paint, adding functionalized microcapsules to the body of paint, provides additional strength and structure to the paint product and increase the strength of the paint. For example, such a paint may further resist tearing or peeling as compared to currently available products.

Similarly, in use in the plastic industry, functionalized microcapsules can impart additional strength while maintaining elasticity or flexibility of a product. Alternatively, in other uses, additional rigidity can be imparted, simply depending on the components within the functionalized microcapsules.

Certainly, such microcapsules can be further utilized in adhesive products, wherein the properties of an adhesive can be manipulated based on the component of a functionalized microcapsule such that the adhesive has greater lateral or shear strength, or has increased flexibility while maintaining a bond. Similarly, other characteristics can be envisioned based on the component of the functionalized microcapsule.

Finally, it the use of such functionalized microcapsules can be facilitated into one of any number of polymer based products. This allows for modification and improvement of any number of materials, including wearable fabrics, ballistic products, solid and rigid products, etc. However, by using the functionalized microcapsules, the character of the polymer can be amended based on the need and ultimate use of the product.

Accordingly, the compositions and materials that can be encapsulated into the various microcapsules are far ranging. These include restorative ions, such as calcium, phosphate, and fluoride, anti-bacterial components such as benzalkonium or cetylpyridinium ions, but may also include other materials. Additional compositions may include other suitable ionic materials, antibacterial materials, whitening materials, and the like. However, in other classes of use, such as in industrial uses, microcapsules may contain other materials to enhance the physical properties of the materials. For example, rubber materials, silicone materials, or other similar natural or synthetic material or polymers that provide for different structural properties. Suitable silicone materials include, but are not limited to those having a molecular weight between about 12,500 and 2,500,000 g/mol.

The use of an inhibitor may be suitable in certain embodiments as a material to prevent autopolymerization in the material.

Accelerator and photosensitizer are frequently used together in photoinitiator chemistry to initiate the polymerization of the material and to accelerate the polymerization. Therefore, the material can be polymerized quickly in certain circumstances, such as when making a dental composite in the mouth.

These components can therefore be imparted into solid, liquid, gels, aerosols and the like. By imparting pre-determined characteristics to the functionalized microcapsules, it is possible to impart pre-determined functionality to such a product.

EXAMPLES

Example 1

Composition of Matter Example 1a (Sealant A, 2 wt % Bondable Microcapsule)

A composition for pit and fissure sealant with remineralization capabilities and enhanced fracture toughness is described as follows. A pit and fissure sealant containing resin (67 wt %), glass fillers (30 wt %), microcapsules with acrylate functionalized surfaces that contain a 5 M aqueous solution of calcium nitrate (2 wt %), and photoinitiators (1 wt %).

Composition of Matter Example 1b (Sealant B, 2 wt % Non-Bondable Microcapsule)

A composition for pit and fissure sealant with remineralization capabilities and enhanced fracture toughness is described as follows. A pit and fissure sealant containing resin (67 wt %), glass fillers (30 wt %), microcapsules without acrylate functionalized surfaces that contain a 5 M aqueous solution of calcium nitrate (2 wt %), and photoinitiators (1 wt %).

Composition of Matter Example 1c (Sealant C, 5 wt % Bondable Microcapsule)

A composition for pit and fissure sealant with remineralization capabilities and enhanced fracture toughness is described as follows. A pit and fissure sealant containing resin (64 wt %), glass fillers (30 wt %), microcapsules with acrylate functionalized surfaces that contain a 5 M aqueous solution of calcium nitrate (5 wt %), and photoinitiators (1 wt %).

Composition of Matter Example 1d (Sealant D, 5 wt % Non-Bondable Microcapsule)

A composition for pit and fissure sealant with remineralization capabilities and enhanced fracture toughness is described as follows. A pit and fissure sealant containing resin (64 wt %), glass fillers (30 wt %), microcapsules without acrylate functionalized surfaces that contain a 5 M aqueous solution of calcium nitrate (5 wt %), and photoinitiators (1 wt %).

Table 1: The fracture toughness for the 4 sealant formulations that contain non-bondable microcapsules as controls and the new bondable microcapsules.

| Sample | Average Fracture Toughness, ($K_{IC}$) |
|---|---|
| 2 w/w % non-bondable microcapsules, control | 1.2 ± 0.2 |
| 2 w/w % bondable microcapsules | 2.0 ± 0.4 |
| 5 w/w % non-bondable microcapsules, control | 1.3 ± 0.3 |
| 5 w/w % bondable microcapsules | 2.0 ± 0.3 |

Accordingly, by addition of bondable microcapsules, the average fracture toughness increases by more than 50% as compared to an equivalent weight % control with non-bondable microcapsules.

Composition of Matter Example 2 (A Plurality of Bondable Microcapsules Containing Different Therapeutic Agents in the Same Formulation)

A composition for pit and fissure sealant with remineralization capabilities and enhanced fracture toughness is described as follows. A pit and fissure sealant containing resin (64 wt %), glass fillers (30 wt %), microcapsules with acrylate functionalized surfaces that contain a 5 M aqueous solution of calcium nitrate (2 wt %), microcapsules with acrylate functionalized surfaces that contain a 6 M aqueous solution of potassium phosphate dibasic (1 wt %), microcapsules with acrylate functionalized surfaces that contain a 0.8 M aqueous solution of sodium fluoride (2 wt %), and photoinitiators (1 wt %).

Composition of Matter Example 3

A composition for pit and fissure sealant with antimicrobial properties and enhanced fracture toughness is described as follows. A pit and fissure sealant containing resin (64 wt %), glass fillers (30 wt %), microcapsules with acrylate functionalized surfaces that contain a 5 w/w % aqueous solution of benzalkonium chloride (5 w/w %), and photoinitiators (1 wt %).

Composition of Matter Example 4

A composition for a dental resin composite with enhanced mechanical properties is described as follows. A resin mixture (16 wt % total) was first made by combining UDMA resin with TEGDMA resin in a 4/1 ratio. A photosensitizer (camphoroquinone) was added at 0.7 wt % of the total composition. An accelerator (ethyl-4-dimethylaminobenzoate) was added at 0.25 wt % of the total composition. The photosensitizer and accelerator are commonly used together in photoinitiator chemistry. An inhibitor (4-methoxyphenol) was added at 0.05 wt % of the total composition. The resin, photosensitizer, accelerator and inhibitor were combined in a flask and mixed at 50° C. Upon homogenization, the above resin blend was mixed with the following fillers (84 wt % total): silanated strontium glass 71 wt %, fumed silica 10 wt %, microcapsules with acrylate functionalized surfaces that contain high molecular weight silicone oil 3 wt %.

Example 5

A composition for a flexible denture base material with enhanced mechanical properties is described as follows. A resin mixture (16 wt % total) was first made by combining UDMA resin with TEGDMA resin in a 4/1 ratio. A photosensitizer (camphoroquinone) was added at 0.7 wt % of the total composition. An accelerator (ethyl-4-dimethylaminobenzoate) was added at 0.25 wt % of the total composition. An inhibitor (4-methoxyphenol) was added at 0.05 wt % of the total composition. The resin, photosensitizer, accelerator and inhibitor were combined in a flask and mixed at 50° C. Upon homogenization, the above resin blend was mixed with the following fillers (30 wt % total): silanated strontium glass 22 wt %, fumed silica 3 wt %, microcapsules with acrylate functionalized surfaces that contain high molecular weight silicone oil 5 wt %.

Although the present invention has been described in considerable detail, those skilled in the art will appreciate that numerous changes and modifications may be made to the embodiments and preferred embodiments of the invention and that such changes and modifications may be made without departing from the spirit of the invention. It is therefore intended that the appended claims cover all equivalent variations as fall within the scope of the invention.

What is claimed is:

1. A composition comprising of a polymeric continuous phase containing a monomer, an initiator, and a microcapsule encapsulating a fluid, wherein said microcapsule has a surface functionalized with a polymerizable functional group comprising a carbon-carbon pi bond capable of polymerizing with said monomer to form a carbon-carbon covalent bond between the polymerizable functional group and the monomer.

2. The composition of claim 1 wherein the fluid comprises a salt solution containing an ion selected from the group consisting of calcium, fluoride, phosphate, benzalkonium, cetylpyridinium, iodide, and combinations thereof.

3. The composition of claim 1 wherein the fluid comprises a combination of salts that result in a buffer solution.

4. The composition of claim 1 wherein the fluid encapsulated within the microcapsule is a silicone.

5. The composition of claim 4, wherein the silicone having a molecular weight between about 12,500 and 2,500,000 g/mol.

6. The composition of claim 1 wherein the fluid encapsulated within the microcapsule is a rubber material.

7. The composition of claim 1 further comprising a glass filler.

8. The composition of claim 1 further comprising an inhibitor.

9. The composition of claim 1 where the fluid is an aqueous solution of a salt containing ions selected from the group consisting of: fluoride, calcium, phosphate, benzalkoniuum, cetylpyridinium, and combinations thereof.

10. The composition of claim 9 comprising a combination of salt ions, wherein the combination of salt ions is achieved by using a plurality of microcapsules that contain either fluoride, or calcium, or phosphate, or benzalkonium, or cetylpyridiniun, and wherein each microcapsule contains only one of the fluoride, calcium, benzalkonium, cetylpyridinium, or phosphate ions.

11. The composition of claim 3 where the buffered solution contains a therapeutic agent.

12. The composition of claim 1 further comprising a photoinitiator.

13. The composition of claim 1 wherein the functional group is an acrylate group.

14. The composition of claim 1, wherein the monomer is TEGDMA, bisGMA, or a combination thereof monomers.

* * * * *